United States Patent
Yamamoto et al.

(10) Patent No.: US 8,147,636 B2
(45) Date of Patent: Apr. 3, 2012

(54) MANUFACTURING METHOD OF ABSORBENT ARTICLE AND MANUFACTURING APPARATUS OF ABSORBENT ARTICLE

(75) Inventors: Hiroki Yamamoto, Kanonji (JP); Yoshihiko Matsumoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 361 days.

(21) Appl. No.: 12/390,040

(22) Filed: Feb. 20, 2009

(65) Prior Publication Data

US 2010/0078127 A1  Apr. 1, 2010

(30) Foreign Application Priority Data

Nov. 11, 2008 (JP) ................ P2008-289310

(51) Int. Cl.
*B32B 37/00* (2006.01)
(52) U.S. Cl. ........ 156/163; 156/160; 156/164; 156/229; 156/494; 156/495; 156/496
(58) Field of Classification Search ................ 156/229, 156/160, 163, 164, 494–496, 161
See application file for complete search history.

(56) References Cited

U.S. PATENT DOCUMENTS

| | | | | |
|---|---|---|---|---|
| 5,389,173 | A * | 2/1995 | Merkatoris et al. | 156/164 |
| 5,660,664 | A * | 8/1997 | Herrmann | 156/161 |
| 6,895,649 | B2 * | 5/2005 | Kojo et al. | 29/407.01 |
| 7,000,260 | B2 * | 2/2006 | Rajala et al. | 2/400 |
| 7,045,031 | B2 * | 5/2006 | Popp et al. | 156/176 |
| 2006/0185135 | A1 * | 8/2006 | Yamamoto et al. | 28/116 |

FOREIGN PATENT DOCUMENTS

| | | | |
|---|---|---|---|
| JP | 2002-35027 A | * | 2/2002 |
| JP | 2004-159866 A | | 6/2004 |
| JP | 2006-214560 A | * | 8/2006 |

OTHER PUBLICATIONS

Machine translation of JP-2006-214560, date unknown.*
Machine translation of JP-2002-35027, date unknown.*

* cited by examiner

*Primary Examiner* — Jeff Aftergut
(74) *Attorney, Agent, or Firm* — Lowe, Hauptman, Ham & Berner, LLP

(57) ABSTRACT

The present invention provides a method includes the steps of: conveying in a conveyance direction MD a second web in which components forming one part of an absorbent article are sequentially arranged; swinging an elastic member in a cross direction CD at a predetermined cycle by using a swing guide mechanism for guiding the elastic member; and pressing, between one pair of press rollers, the second web on which the elastic member is arranged. The swing guide mechanism has a motor with a rotational shaft, an arm member for guiding the elastic member to a predetermined position on the second web in the cross direction, and a speed reducer provided between the rotational shaft and a base of the arm member to make a rotational speed of the arm member slower than a rotational speed of the rotational shaft.

16 Claims, 8 Drawing Sheets

MANUFACTURING METHOD OF ABSORBENT ARTICLE AND MANUFACTURING APPARATUS OF ABSORBENT ARTICLE

BACKGROUND OF THE INVENTION

1. Field of the Invention

The present invention relates to a manufacturing method of an absorbent article and a manufacturing apparatus of an absorbent article, in which a filiform elastic member is arranged in a cross direction crossing a predetermined direction, at least partially in a front waistline region, a back waistline region, and a crotch region.

2. Description of the Related Art

Conventionally, the manufacturing process of an absorbent article such as a disposable diaper widely uses a method of arranging a filiform elastic member (rubber) having stretching properties at least partially in a front waistline region, back waistline region, and crotch region of the absorbent article, in order to improve the fittingness to a wearing target (for example, a human body).

Specifically, in the manufacturing process, the elastic member is arranged in a waveform on a web in which components forming one part of the absorbent article, such as a back sheet or an absorbent sheet are sequentially arranged. That is, the filiform elastic member is arranged in a waveform on a crosswise-flow web in which the longitudinal direction of the absorbent article is arranged along a cross direction (CD) crossing a conveyance direction (Machine Direction (MD)) of the web. Accordingly, the absorbent articles each provided with a gather corresponding to the shape of the crotch region can be continuously manufactured.

As such a method of arranging a filiform elastic member in a waveform on a web being conveyed, known is a method of feeding an elastic member from an tip end portion of an arm member which is directly connected with a rotational shaft of a servomotor, while swinging the arm member in width directions of the web at a predetermined cycle (for example, see Japanese Patent Application Publication No. 2004-159866 (pages 6 to 8, FIGS. 3 and 4)). Since the servomotor is rotatable at high speed, use of such an arm member directly connected with the servomotor leads to improvement of a production rate of the absorbent article.

However, the above-described conventional manufacturing method of an absorbent article has the following problem. Specifically, when an absorbent article with a larger size, for example, a disposable diaper for adults is to be manufactured, an arm member has to be increased in length than that for a disposable diaper for infants. However, the increase in length of the arm member brings about an increase of a weight thereof, thereby posing a problem that it is difficult to rotate the servomotor at desired speed.

On the other hand, the arm member may be manufactured with a longer length but light weight. In this case, however, rotating the arm member at a desired speed may damage the arm member, because the arm member itself cannot endure the acceleration.

SUMMARY OF THE INVENTION

Thus, the present invention has been made in light of the foregoing situation. Accordingly, an object of the present invention is to provide a manufacturing method of an absorbent article and a manufacturing apparatus of an absorbent article, which enables improvement of a production rate while securely reducing damages of an arm member and which is capable of manufacturing absorbent articles of various sizes.

To solve the above-described problem, the present invention includes the following aspect. Firstly, a first aspect of the present invention provides a manufacturing method of an absorbent article (absorbent article 1) which includes a front waistline region (front waistline region 10), a back waistline region (back waistline region 20), and a crotch region (crotch region 30) positioned between the front waistline region and the back waistline region and has a filiform elastic member (elastic member 6') arranged at least partially in the front waistline region, the back waistline region, and the crotch region in a cross direction (CD) crossing a predetermined direction (Machine Direction (MD)). The manufacturing method of an absorbent article includes the steps of conveying in the predetermined direction a web (for example, a second web 7B) in which components forming one part of the absorbent article are sequentially arranged, swinging, the elastic member by using a guide arm unit (swing guide mechanism 120) guiding the elastic member, at a predetermined cycle in the cross direction crossing the web being conveyed in the predetermined direction, and pressing, between one pair of press rollers (an upper press roller 130A and a lower press roller 130B), the web on which the elastic member is arranged, in which the guide arm unit has a motor (motor 210) with a rotational shaft (rotational shaft 211), an arm member (arm member 220) guiding the elastic member to a predetermined position on the web in the cross direction, and a speed reducer (speed reducer 230) provided between the rotational shaft and a base (base 221) of the arm member to make a rotational speed ($V_3$) of the arm member slower than a rotational speed ($V_2$) of the rotational shaft.

The aspect of the present invention can provide a manufacturing method of an absorbent article and a manufacturing apparatus of an absorbent article, which improve a production rate while securely reducing damages of an arm member and which can deal with various sizes.

DESCRIPTION OF THE PREFERRED EMBODIMENT

Figure 1:
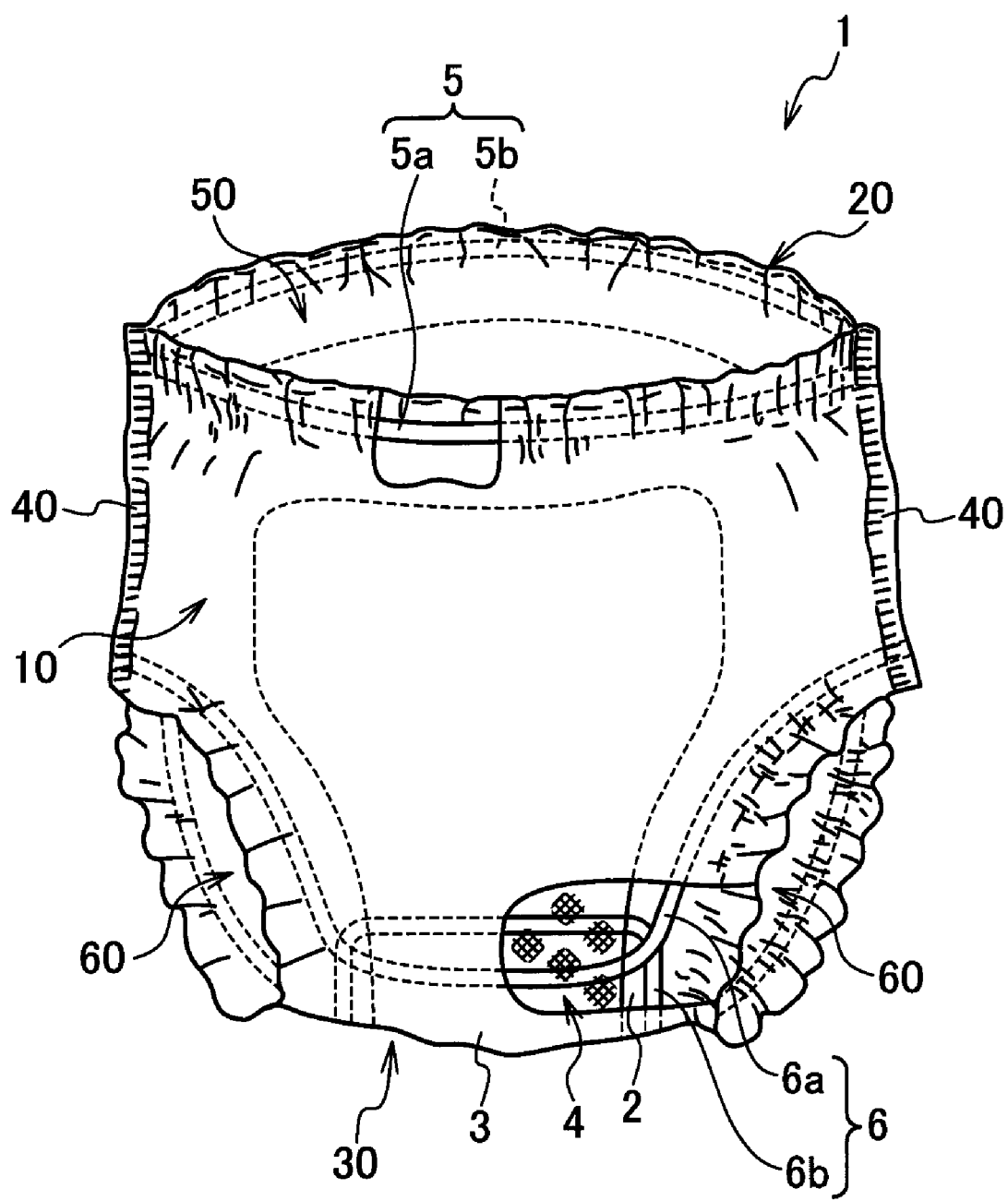
FIG. 1 is a perspective view showing an absorbent article according to the present embodiment.

A manufacturing method of an absorbent article according to the present invention will be described below by referring to the drawings. Specifically, the description will be given of the following points: (1) Configuration of Absorbent Article, (2) Manufacturing Method of Absorbent Article, (3) Configuration of Elastic Member Fixing Apparatus, (4) Configuration of Swing guide mechanism, (5) Operation of Elastic Member Fixing Apparatus, (6) Advantages and Effects, (7) Modified Examples, and (8) Other Embodiments.

In the following description of the drawings, same or similar reference symbols are given to denote same or similar portions. However, it should be noted that the drawings are schematic and ratios of dimensions and the like are different from actual ones.

Therefore, specific dimensions and the like should be determined by taking into consideration the following description. Moreover, as a matter of course, also among the drawings, there are included portions in which dimensional relationships and ratios are different from each other.

(1) CONFIGURATION OF ABSORBENT ARTICLE

Firstly, a configuration of an absorbent article according to the present embodiment will be described by referring to the drawings. FIG. 1 is a perspective view showing an absorbent article according to the present embodiment. In the present embodiment, an absorbent article 1 is a disposable diaper for adults.

As shown in FIG. 1, the absorbent article 1 is mainly formed of a liquid permeable front sheet 2 which comes in contact with a skin of a wearing target (hereinafter, a wearer), a back sheet 3 provided at the outer side of the front sheet 2, and an absorber 4 which is provided between the front sheet 2 and the back sheet 3, and absorbs dejects from the wearer.

In addition, a liquid impermeable waterproof sheet (unillustrated) is provided between the back sheet 3 and the absorber 4. That is, the absorber 4 is provided between the front sheet 2 and the waterproof sheet.

As the front sheet 2, employed is a nonwoven fabric, a perforated plastic film, or the like. As the back sheet 3, employed is a nonwoven fabric. As the absorber 4, employed is ground pulp, a mixture of ground pulp and high absorbent polymer particles, or the like. As the waterproof sheet, employed is a plastic, a nonwoven fabric, a mixed sheet of a plastic film and a nonwoven fabric, or the like.

The absorbent article 1 has a front waistline region 10 corresponding to a front waistline of the wearer, a back waistline region 20 corresponding to a back waistline of the wearer, and a crotch region 30 corresponding to a crotch of the wearer.

The front waistline region 10 and the back waistline region 20 are integrated by connecting portions 40. A waist gather 5 made of a filiform rubber or the like having stretching properties is provided at the peripheries of the front waistline region 10 and the back waistline region 20. The waist gather 5 includes a front waist gather 5a positioned in the front waistline region 10 and a back waist gather 5b positioned in the back waistline region 20. A waistline opening region 50 is formed between the front waist gather 5a and the back waistline gather 5b.

The front waistline region 10 and the back waistline region 20 have stretching properties in a conveyance direction MD of a first web 7A used to form the front sheet 2 and a second web 7B (see, FIG. 2) used to form the back sheet 3. For example, the front waistline region 10 and the back waistline region 20 may be elastic in the conveyance direction MD by providing the waist gather 5 therein or may be elastic in the conveyance direction MD by forming the front waistline region 10 and the back waistline region 20 themselves with elastic sheets.

The crotch region 30 is provided between the front waistline region 10 and the back waistline region 20. Leg gathers 6, each formed of a filiform rubber having stretching properties or the like, are formed on both sides of the crotch region 30. The leg gather 6 includes a front leg gather 6a positioned closer to the front waistline region 10 and a back leg gather 6b positioned closer to the back waistline region 20. Leg circumferential opening regions 60 are formed at portions which are between the front leg gather 6a and the back leg gather 6b and on the both sides of the crotch region 30.

The crotch region 30 is elastic in the cross direction CD (CD) crossing the conveyance direction MD. For example, the crotch region 30 may be elastic in the cross direction CD by providing the leg gather 6 therein or may be elastic in the cross direction CD by forming the crotch region 30 itself with an elastic sheet.

(2) MANUFACTURING METHOD OF ABSORBENT ARTICLE

Figure 2:
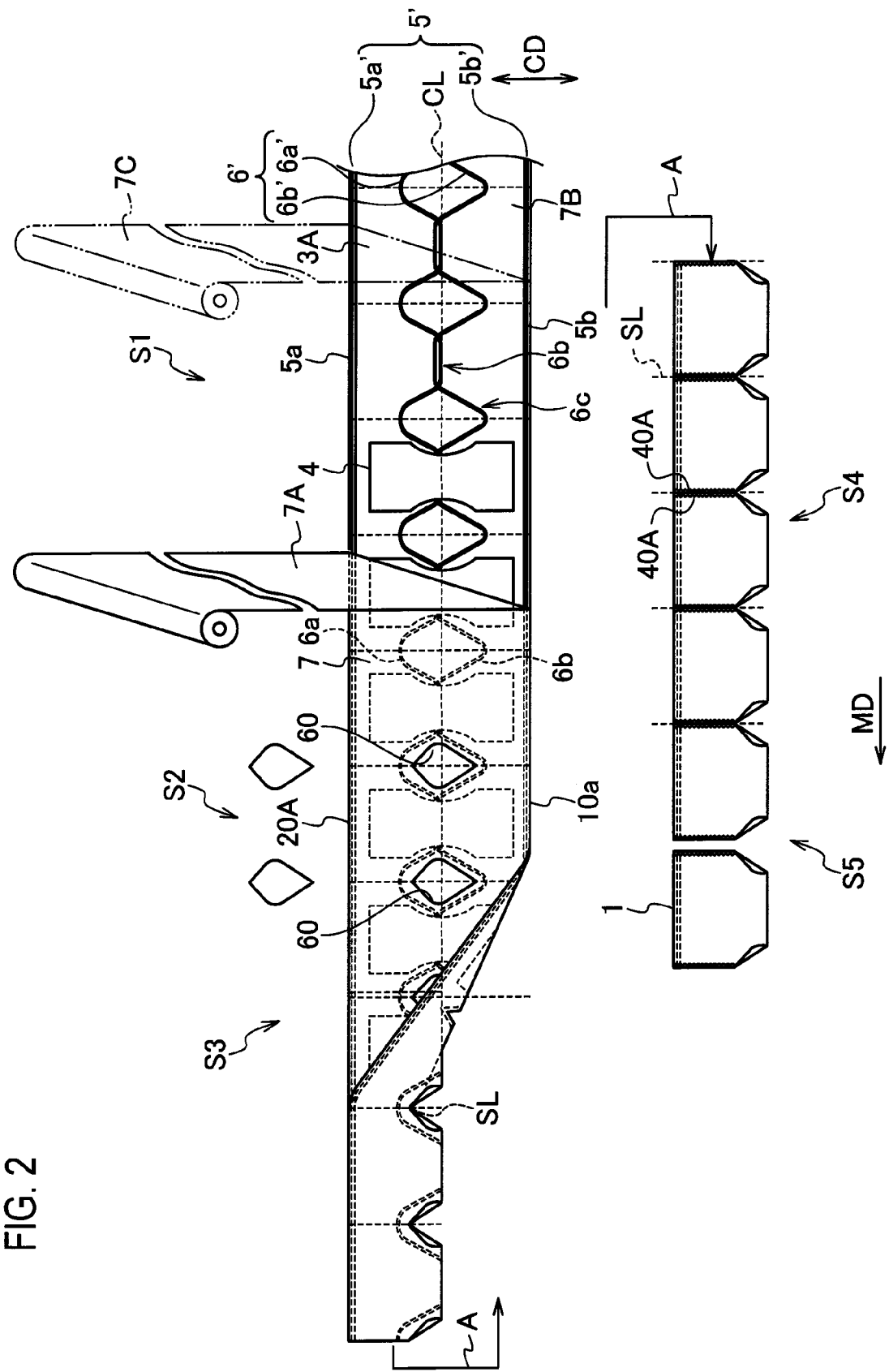
FIG. 2 is a view for illustrating one part of a manufacturing method of an absorbent article according to the present embodiment.

Next, a configuration of a manufacturing method of an absorbent article according to the present embodiment will be described by referring to the drawings. FIG. 2 is a view for illustrating a part of a manufacturing method of an absorbent article according to the present embodiment.

As shown in FIG. 2, the manufacturing method of an absorbent article includes at least a component mounting process, a leg circumference forming process, a folding process, a connecting process, and a cutting process. Note that processes of conveying webs in the conveyance direction MD (predetermined direction) are included between the individual processes by using an unillustrated conveyance apparatus (for example, a belt conveyance apparatus). The webs conveyed here are the liquid permeable first web 7A used to form the front sheet 2, the liquid impermeable second web 7B used to form the back sheet 3, and a third web 7C which is formed of the same material or the like as that of the second web 7B and is used to form the back sheet 3.

(2-1) Component Mounting Process

In the component mounting process S1, components constituting the absorbent article 1, such as the elastic member, the third web 7C, the waterproof sheet (unillustrated), the absorber 4, and the first web 7A are mounted on the second web 7B.

Specifically, firstly, the elastic member 5' forming the waist gather 5 in a stretched state is linearly mounted in the positions corresponding to the front waistline region 10 and the back waistline region 20 on the second web 7B. That is, the elastic member 5a' forming the front waist gather 5a and the elastic member 5b' forming the back waist gather 5b are mounted in the positions corresponding to the front waistline region 10 and the back waistline region 20 on the second web 7B. With this configuration, the waist gather 5 (the front waistline gather 5a and the back waist gather 5b) is formed in the positions corresponding to the front waistline region 10 and the back waistline region 20 on the second web 7B.

Secondly, the third web 7C is mounted on the second web 7B. At this time, the elastic member 6' forming the leg gather 6 in the stretched state is arranged in the position corresponding to the crotch region 30 on the second web 7B and the third web 7C while swinging at a predetermined cycle in the cross direction CD. Then, the elastic member 6' is held between the second web 7B and the third web 7C to form the leg gather 6 (the front leg gather 6a and the back leg gather 6b).

Note that the second web 7B and the third web 7C which hold the elastic member 6' therebetween are pressed by an upper press roller 130A and a lower press roller 130B which will be described later.

The elastic member 6a' forming the front leg gather 6a and the elastic member 6b' forming the back leg gather 6b form a large ring portion 6C and a small ring portion 6d which has a smaller size in the cross direction CD than that of the large ring portion 6c.

As described above, after arranging the elastic member 6a' on the second web 7B and the third web 7C, the second web 7B and the third web 7C are pressed by the upper press roller 130A and the lower press roller 130B. At this time, if a position in which the small ring portion 6d is designed to be formed is not pressed, the elastic member 6a'' is not fixed in the designed position on the web. The elastic member 6a' is arranged in the stretched state, so that it contracts in the position where the elastic member 6a' is not fixed on the web and thus forms a substantially straight line from a predetermined arranged shape. In this manner, the small ring portion 6d is formed.

The same holds for a case where an adhesive is not applied to the designed position. In the position where the adhesive is not designed to be applied, the elastic member 6a' is not fixed on the web. Accordingly, the small ring portion 6d can be similarly formed.

Thirdly, the waterproof sheet (unillustrated) and the absorber 4 are mounted on the second web 7B and the third web 7C with the elastic member 6' being held therebetween so as to be uniformly spaced in the conveyance direction MD. The waterproof sheet may be mounted on the second web 7B and the third web 7C in a state being connected with the absorber 4 in advance, or may be mounted on the second web 7B and the third web 7C in a state being separated from the absorber 4.

Fourthly, the first web 7A forming the front sheet 2 overlaps the second web 7B and the third web 7C on which the components forming the absorbent article 1 are mounted.

Note that, the component mounting process S1 does not necessarily have to be performed in the order of the first step to the fourth step. The order may be changed if needed.

(2-2) Leg Circumference Forming Process

In the leg circumference forming process S2, after the component mounting process S1, an inner circumferential side of the large ring portion 6c is cut out on the second web 7B and the first web 7A with the components being held therebetween (hereinafter, a composite web 7) to form the leg circumference opening region 60 (so-called, a leg hole).

(2-3) Folding Process

In the folding process S3, after the leg circumference forming process S2, the composite web 7 is folded in two along the center line CL which passes through the center of the composite web 7 in the cross direction CD and extends in the conveyance direction MD. That is, a side edge 10A of the composite web 7 corresponding to the front waistline region 10 and a side edge 20A of the composite web 7 corresponding to the back waistline region 20 overlap each other being flush with each other.

(2-4) Connecting Process

In the connecting process S4, after the folding process S3, predetermined regions 40A corresponding to the connecting portions 40 of the absorbent article are connected with supersonic treatment or heat treatment. The predetermined regions 40A show both sides of a virtual line SL in the conveyance direction MD, which extends in the cross direction CD and shows a position designed to be cut.

(2-5) Cutting Process

In the cutting process S5, after the connecting process S4, the composite web 7 with the predetermined regions 40A connected is cut along the virtual line SL. In doing so, the absorbent article 1 is formed.

(3) CONFIGURATION OF ELASTIC MEMBER FIXING APPARATUS

Figure 3:
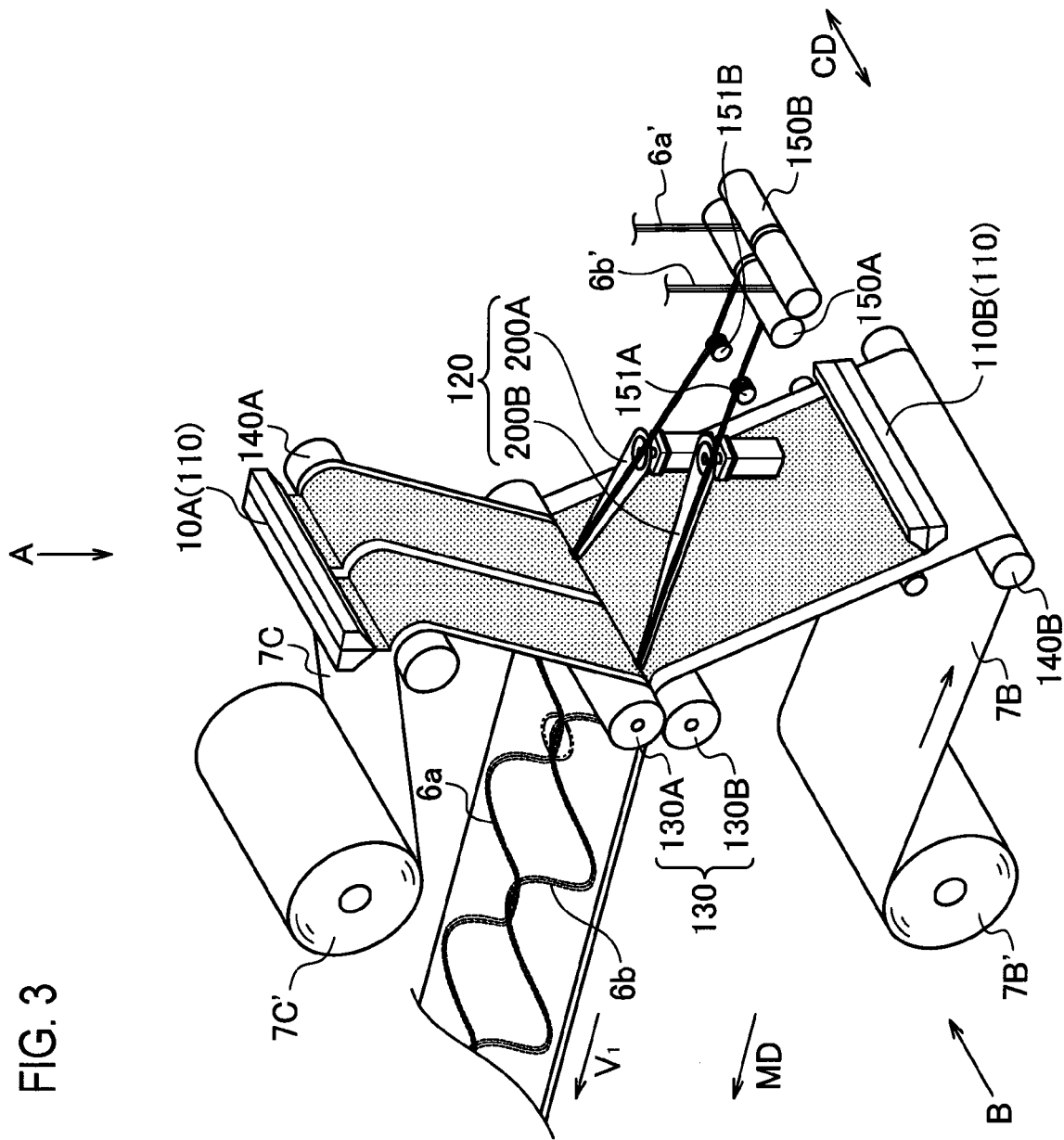
FIG. 3 is a perspective view showing an elastic member fixing apparatus according to the present embodiment.
Figure 4:
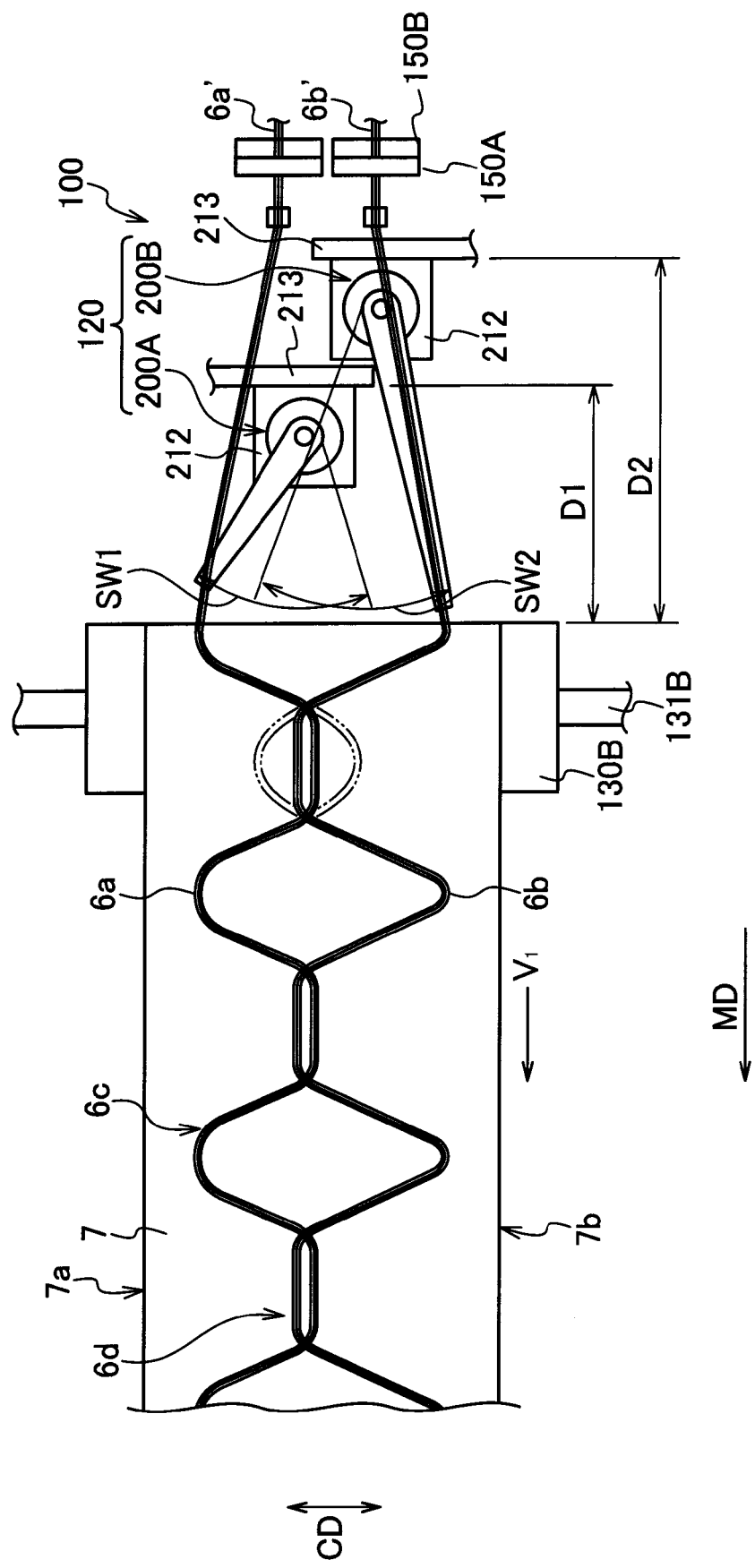
FIG. 4 is a top view (a view seen in the direction of the arrow A in FIG. 3) showing the elastic member fixing apparatus according to the present embodiment.
Figure 5:
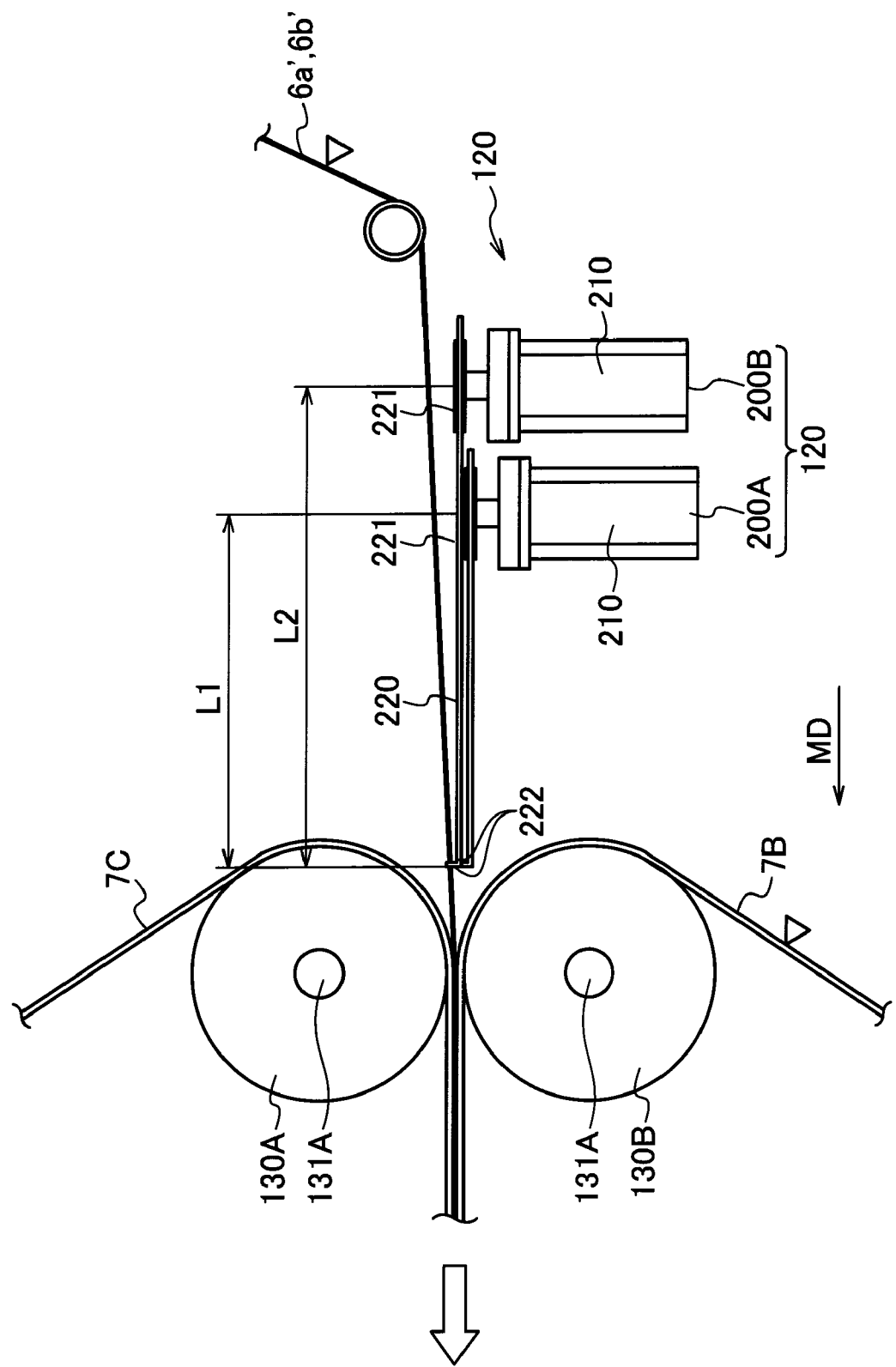
FIG. 5 is a side view (a view seen in the direction of the arrow B in FIG. 3) showing the elastic member fixing apparatus according to the present embodiment.

Next, the configuration of an elastic member fixing apparatus (manufacturing apparatus of an absorbent article) which is used in the above-described component mounting process will be described by referring to the drawings. FIG. 3 is a perspective view showing an elastic member fixing apparatus according to the present embodiment. FIG. 4 is a top view (a view seen in the direction of the arrow A in FIG. 3) showing the elastic member fixing apparatus according to the present embodiment. FIG. 5 is a side view (a view seen in the direction of the arrow B in FIG. 3) showing the elastic member fixing apparatus according to the present embodiment.

As shown in FIGS. 3 to 5, the elastic member fixing apparatus 100 swings the elastic member 6' forming the leg gather 6 in the cross direction CD at a predetermined cycle so as to arrange the elastic member 6' between the second web 7B and the third web 7C. That is, the elastic member fixing apparatus 100 arranges the elastic member 6' in a curved state between the second web 7B and the third web 7C to form the leg gather 6 (the front leg gather 6a and the back leg gather 6b).

The elastic member fixing apparatus 100 includes at least a web feeding mechanism (unillustrated), a gather feeding mechanism (unillustrated), an adhesive applying mechanism 110, a swing guide mechanism 120 (guide arm portion), and a press roller mechanism 130.

(3-1) Web Feeding Mechanism

The web feeding mechanism sequentially feeds a web from a jumbo roll. Specifically, the web feeding mechanism has an upper web feeding mechanism which sequentially feeds the third web 7C from a web jumbo roll 7C' and a lower web feeding mechanism which sequentially feeds the second web 7B from a second web jumbo roll 7B'.

The upper web feeding mechanism and the lower web feeding mechanism sequentially feed the second web 7B and the third web 7C to the press roller mechanism 130 through rollers 140A and 140B which rotate around rotation shafts (unillustrated) provided along the cross direction CD.

(3-2) Gather Feeding Mechanism

The gather feeding mechanism sequentially feeds the elastic member 6' forming the leg gather 6 from a jumbo roll. Specifically, the gather feeding mechanism has a front gather feeding mechanism which sequentially feeds the elastic member 6a' forming the front leg gather 6a from a jumbo roll (unillustrated) and a back gather feeding mechanism which sequentially feeds the elastic member 6b' forming the back leg gather 6b from a jumbo roll (unillustrated).

The front gather feeding mechanism and the back gather feeding mechanism sequentially feed the leg gather 6 to the press roller mechanism 130 through feed rollers 150A and 150B which rotate around the rotation shafts (unillustrated) provided along the cross direction CD and line-dividing rollers 151A and 151B which divide the elastic member 6a' and the elastic member 6b'.

(3-3) Adhesive Applying Mechanism

The adhesive applying mechanism is a spray-type device for applying an adhesive (for example, a hot-melt adhesive) onto a web. Specifically, the adhesive applying mechanism 110 has an upper adhesive applying mechanism 110A which applies an adhesive onto the third web 7C and a lower adhesive applying mechanism 110B which applies an adhesive onto the second web 7B.

Note that the upper adhesive applying mechanism 110A applies an adhesive onto a surface of the third web 7C except the center portion thereof. On the other hand, the lower adhesive applying mechanism 110B applies an adhesive onto an entire surface of the second web 7B.

(3-4) Swing Guide Mechanism

The swing guide mechanism 120 swings the elastic member 6' forming the leg gather 6 in the cross direction CD at a predetermined cycle. The swing guide mechanism 120 has a first swing guide mechanism 200A which swings the elastic member 6a' forming the front leg gather 6a and a second swing guide mechanism 200B which swings the elastic member 6b' forming the back leg gather 6b. The swing guide mechanism 120 will be described later in detail.

(3-5) Press Roller Mechanism

The press roller mechanism 130 presses the second web 7B and the third web 7C with the elastic member 6' being held between the second web 7B and the third web 7C. Specifically, the press roller mechanism 130 has an upper press roller 130A which comes in contact with the third web 7C and a lower press roller 130B which comes in contact with the second web 7B.

The upper press roller 130A rotates around the rotation shaft 131A provided along the cross direction CD. Similarly, the lower press roller 130B rotates around the rotation shaft 131B provided along the cross direction CD. The elastic member 6' is guided by the swing guide mechanism 120 to a position where the upper press roller 130A and the lower press roller 130B come closest to each other.

(4) CONFIGURATION OF SWING GUIDE MECHANISM

Figure 6:
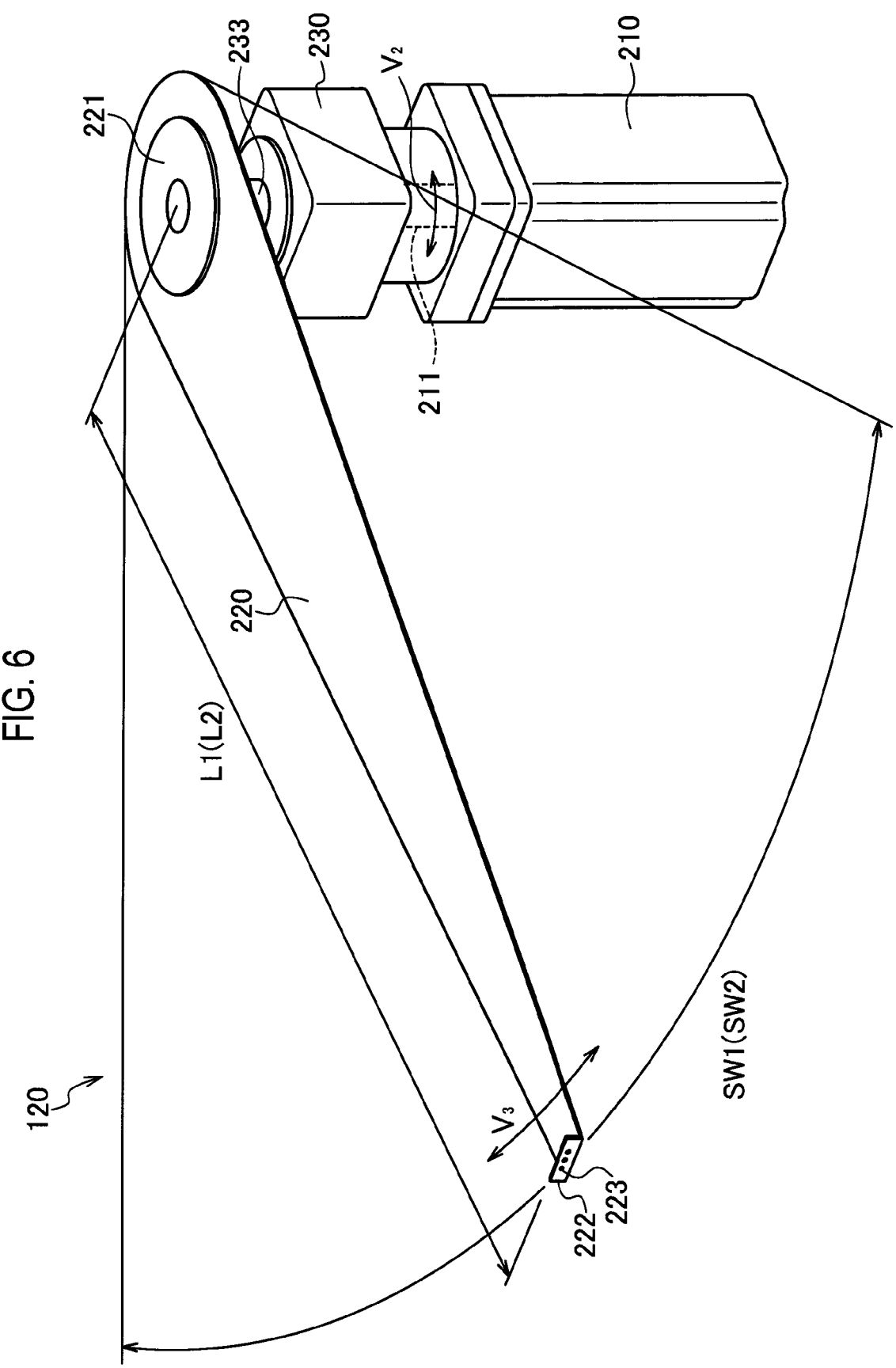
FIG. 6 is a perspective view showing a swing guide mechanism according to the present invention.
Figure 7:
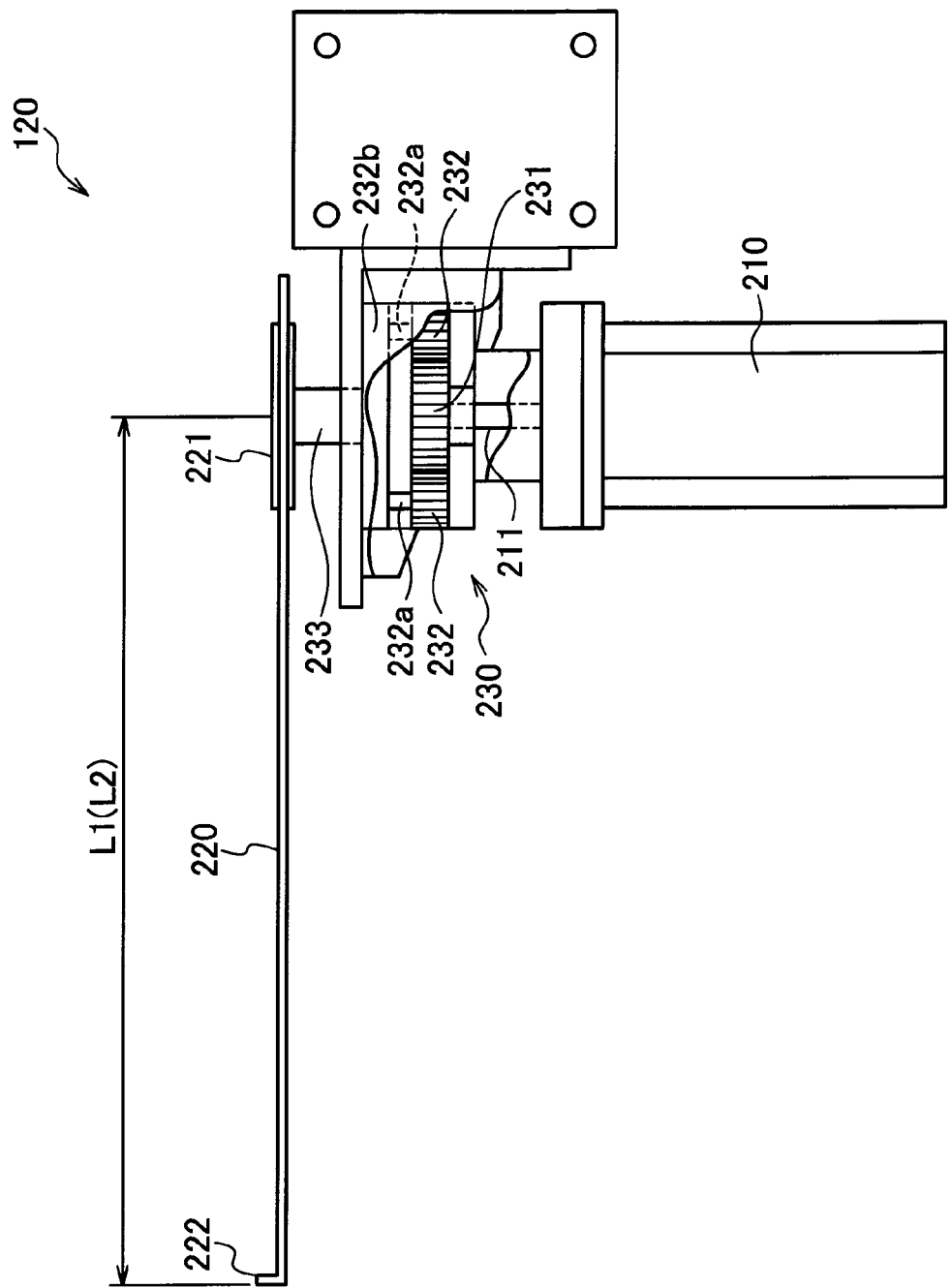
FIG. 7 is a side view showing the swing guide mechanism according to the present invention.

Next, the configuration of the swing guide mechanism 120 which is a characteristic of the present invention will be described by referring to FIGS. 3 to 8. FIG. 6 is a perspective view showing a swing guide mechanism according to the present embodiment. FIG. 7 is a side view showing the swing guide mechanism according to the present embodiment.

Note that the first swing guide mechanism 200A and the second swing guide mechanism 200B basically have similar configurations, except that arm members 220 to be described later have different lengths. For this reason, the first swing guide mechanism 200A and the second swing guide mechanism 200B are described together as the swing guide mechanism 120.

As shown in FIGS. 3 to 7, the swing guide mechanism 120 has a motor 210 with a rotational shaft 211, an arm member 220 guiding the elastic member 6' to a predetermined position in the cross direction CD between the second web 7B and the third web 7C, and a speed reducer 230 provided between the rotational shaft 211 and a base 221 of the arm member 220.

(4-1-1) Motor

The motor 210 is formed of a servomotor which is operated by a controller into which a program is inputted. This program is capable of causing the elastic member 6' to have a predetermined extension magnification and arranging the elastic member 6' in a desired layout according to a conveyance speed ($V_1$) of the web.

The program operating the motor 210 of the first swing guide mechanism 200A is different from the program operating the motor 210 of the second swing guide mechanism 200B. That is, the predetermined extension magnification and the layout in the front leg gather 6a are different from the predetermined extension magnification and the layout in the back leg gather 6b.

The motor 210 is attached to a base plate 213 through a bracket 212 (see, FIG. 4). In the base plate 213, the motor 210 is movable in the cross direction CD if needed. When D1 denotes a distance to the press roller mechanism 130 from the base plate 213 equipped with the motor 210 of the first shaking guide mechanism 200A, and D2 denotes a distance to the press roller mechanism 130 from the base plate 213 equipped with the motor 210 of the second shaking guide mechanism 200B, the distances D1 and D2 are different from each other.

(4-1-2) Arm Member

The arm member 220 forms a plate shape tapered from the base 221 to a tip end portion 222. It is preferable that the arm member 220 be horizontally arranged (see, FIG. 5).

The arm member 220 is formed by using a metal steel plate. For example, the arm member 220 is formed by using a stainless steel plate.

The tip end portion 222 of the arm member 220 is folded towards an opposite side of the arm member 220 from the side on which the motor 210 is positioned. The tip end portion 222 of the arm member 220 has an insertion hole 223 formed therein, the leg gather 6 inserted into the insertion hole 223.

In the present embodiment, the first swing guide mechanism 200A and the second swing guide mechanism 200B are different in length of the arm members 220. The length L2 of the arm member 220 of the second swing guide mechanism 200B is longer than the length L1 of the arm member 220 of the first swing guide mechanism 200A. On the other hand, the distance from the press roller mechanism 130 to the tip end portion 222 of the first swing guide mechanism 200A is same as distance from the press roller mechanism 130 to the tip end portion 222 of the second swing guide mechanism 200B. For this reason, the relationship between the above-described distance D1 and distance D2 is D2>D1.

For example, the length L1 of the arm member 220 of the first swing guide mechanism 200A is 450 mm (see, FIGS. 5 to 7). On the other hand, the length L2 of the arm member 220 of the second swing guide mechanism 200B is 600 mm (see, FIGS. 5 to 7).

Note that the length of the arm member 220 means here a length form the tip end portion 222 of the arm member 220 to the rotational shaft of the arm member 220.

The weight of the arm member 220 of the first swing guide mechanism 200A is 300 g. On the other hand, the weight of the arm member 220 of the second swing guide mechanism 200B is 400 g.

The amplitude SW1 of the tip end portion 222 of the arm member 220 of the first swing guide mechanism 200A along the cross direction CD is 200 mm (see FIGS. 4 and 6). On the other hand, the amplitude SW2 of the tip end portion 222 of the arm member 220 of the second swing guide mechanism 200B along the cross direction CD is 350 mm (see FIGS. 4 and 6).

(4-1-3) Speed Reducer

The speed reducer 230 makes a rotational speed ($V_3$) of the arm member 220 slower than a rotational speed ($V_2$) of the rotational shaft 211 of the motor 210. Specifically, the speed reducer 230 reduces the rotational speed ($V_3$) of the tip end portion 222 of the arm member 220 from which the leg gather 6 is fed, down to 1/S of the rotational speed ($V_2$) of the rotational shaft 211 of the motor 210, where S is a natural number no fewer than 1, no more than 8.

The speed reducer 230 is formed of a planet gear mechanism (so-called a planetary gear structure). That is, as shown in FIG. 7, the speed reducer 230 has a sun gear 231 positioned in the center and multiple planet gears 232 which revolve and rotate around the sun gear 232.

The speed reducer 230 is directly connected with the rotational shaft 211 of the motor 210 and the base 221 of the arm member 220. Specifically, the sun gear 231 is directly connected with the rotational shaft 211 of the motor 210. On the other hand, a center shaft of a plate 232b to be connected with rotating shafts 232a of the multiple plant gears 232 (that is, the revolution shaft of the plant gear 232) is directly connected with the base 221 of the arm member 220. In other words, the rotational shaft 233 of the speed reducer 230 (that is, the revolution shaft of the plant gear 232) and the rotational shaft 211 of the motor 210 are coaxially positioned.

(5) OPERATION OF ELASTIC MEMBER FIXING APPARATUS

Next, the operation of the elastic member fixing apparatus 100 according to the present embodiment will be described by referring to FIGS. 3 to 5.

The third web 7C is fed from the third web jumbo roll 7C' by the upper web feeding mechanism and the moving direction thereof is changed by the roller 140A. Onto a surface of the third web 7C whose moving direction is changed which faces to the second web 7B, an adhesive is applied by the upper adhesive applying mechanism 110A. At this time, the upper adhesive applying mechanism 110A applies an adhesive onto the surface of the third web 7C except the center portion thereof. The third web 7C onto which the adhesive is applied is supplied between the upper press roller 130A and the lower press roller 130B from above.

Similarly, the second web 7B is fed from the second web jumbo roll 7B' by the lower web feeding mechanism and the moving direction thereof is changed by the roller 140B. Onto the surface of the second web 7B whose moving direction is changed which faces to the third web 7C, an adhesive is applied by the lower adhesive applying mechanism 110B. The second web 7B onto which the adhesive is applied is supplied between the upper press roller 130A and the lower press roller 130B from below.

The elastic member 6a' is fed from the jumbo roll (unillustrated) by the front gather feeding mechanism and is caused to turn the moving direction thereof by the feed roller 150A. The elastic member 6a' turned by the feed roller 150A is divided by the line-dividing roller 151A. The divided elastic member 6a' is caused to swing by the first swing guide mechanism 200A in the cross direction CD at a predetermined cycle. Accordingly, the elastic member 6a' is arranged in a curved shape between the second web 7B and the third web 7C to form the front leg gather 6a.

Similarly, the elastic member 6b' is fed from the jumbo roll (unillustrated) by the back gather feeding mechanism and is caused to turn the moving direction thereof by the feed roller 150B. The elastic member 6b' turned by the feed roller 150B is divided by the line-dividing roller 151B. The divided elastic member 6b' is caused to swing by the second swing guide mechanism 200B in the cross direction CD at a predetermined cycle. Accordingly, the elastic member 6b' is arranged in a curved shape between the second web 7B and the third web 7C to form the back leg gather 6b.

The elastic member 6a' and the elastic member 6b' are pressed by the upper press roller 130A and the lower press roller 130B in a state of being held between the second web 7B and the third web 7C onto which an adhesive is applied. For this reason, the elastic member 6a' and the elastic member 6b' are adhered between the second web 7B and the third web 7C in a state of being caused to swing by the swing guide mechanism 120, so that the above-described large ring portion 6C is formed. On the other hand, even when the elastic member 6a' and the elastic member 6b' are arranged between the second web 7B and the third web 7C, the small ring portion 6d is formed with the generation of resilience in the elastic member 6a' and the elastic member 6b', since the adhesive is not applied to the center portion of the third web 7C.

(6) ADVANTAGES AND EFFECT

According to the present embodiment, the swing guide mechanism 120 (guide arm unit) has the speed reducer 230 which makes the rotational speed ($V_3$) of the arm member 220 slower than the rotational speed ($V_2$) of the rotational shaft 211 of the motor 210. With this, even in a case where the weight of the arm member 220 is increased as the arm member 220 becomes longer, moment of inertia of the arm member 220 on the motor 210 is reduced. Therefore, without limiting the responsiveness of the motor 210, damages of the arm member 220 can be securely reduced. Accordingly, the motor 210 can be rotated at a desired speed and a production rate can be improved. In addition, the motor 210 can of course rotate at high speed the arm member to be used when a disposable diaper for infants is manufactured, and can also employ the long arm member 220 to be used when a disposable diaper for adults is manufactured. That is, the motor 210 can be applicable to disposable diapers in various sizes.

Here, depending on the length of the arm member, a motor with high performance (inertia-resistant weight) may be possibly used. However, the motor becomes unnecessarily large for necessary torque and the moment of inertia of the motor itself is also increased. This results in a disadvantage in control which is required to be highly responsive. For this reason, studied is a method in which the moment of inertia of the arm member 220 on the motor 210 is reduced.

Consider a case of a motor whose specifications are same as those of the motor 210 but without a speed reducer 230. When the motor 210 rotates at high speed in a case where the weight of the arm member is increased as the arm member becomes longer, excessively large moment of inertia of the arm member 220 acts on the motor 210. For this reason, the motor cannot accurately follow specified movement of the arm member, thereby becoming difficult to control the arm member which is rotating at high speed. In addition, by use of the motor, it becomes difficult to arrange the leg gather 6 in a desired curved shape.

On the other hand, consider a case of a motor 210 whose specifications are same as those of the motor. Even when the motor 210 rotates at high speed in a case where the weight of the arm member 220 is increased as the arm member 220 becomes longer, since the speed reducer is provided, the rotational speed ($V_3$) of the tip end portion 222 of the arm member 220 from which the leg gather 6 is fed is reduced relative to the rotational speed ($V_2$) of the rotational shaft 211 of the motor 210. For this reason, as to the motor 210, less moment of inertia of the arm member 220 acts on the rotational shaft 211 of the motor 210 than on the motor 210 without the speed reducer 230. Accordingly, the motor 210 can accurately follow specified movement of the arm member 220, thereby being capable of more securely controlling the arm member 220 which is rotating at high speed. In addition, it becomes easier to arrange the leg gather 6 in a desired curved shape.

According to the present embodiment, the speed reducer 230 reduces the rotational speed ($V_3$) of the tip end portion 222 of the arm member 220 from which the leg gather 6 is fed so as to be 1/S of the rotational speed ($V_2$) of the rotational shaft 211 of the motor 210, where S is a natural number no fewer than 1, no more than 8. With this, less load acts on the motor 210, the motor 210 can accurately follow the specified movement of the arm member 220, and the arm member 220 being rotating at high speed can be securely controlled.

According to the present embodiment, the rotational shaft 233 of the speed reducer 230 (that is, the revolution shaft of the plant gear 232) and the rotational shaft 211 of the motor 210 are coaxially positioned. With this, as compared with the case where the rotational shaft 233 and the rotational shaft 211 are not coaxially positioned, space can be reduced and rigidity of the rotational shaft 211 of the motor 210 can be ensured. For this reason, even when the heavy long arm member 220 is used, the motor 210 easily rotates the arm member 220 at high speed (that is, it becomes easier to repeat reciprocal turning movement of the arm member 220), so that a production rate can be further improved.

According to the present embodiment, the arm member 220 is formed of a metal steel plate. With this, a heavy metal steel plate which can not be used for a motor without a speed reducer, can be used for the motor 210 which can reduce the moment of inertia of the arm member 220 using the speed reducer. Thus, for example, the strength of the arm member 220 is improved more than that of the arm member formed of a carbon fiber, so that durability of the arm member 220 is improved.

(7) MODIFIED EXAMPLE

The arm member 220 according to the above-described embodiment may be modified as below. It should be noted that same reference symbols are given to denote portions same as those of the swing guide mechanism 120 according to the above-described embodiment and different portions will be mainly described.

The swing guide mechanism 120 according to the above-described embodiment is in a plate shape. In contrast, a swing guide mechanism 120A according to a modified example is in a plate shape in which multiple circular holes 225 are formed.

Figure 8:
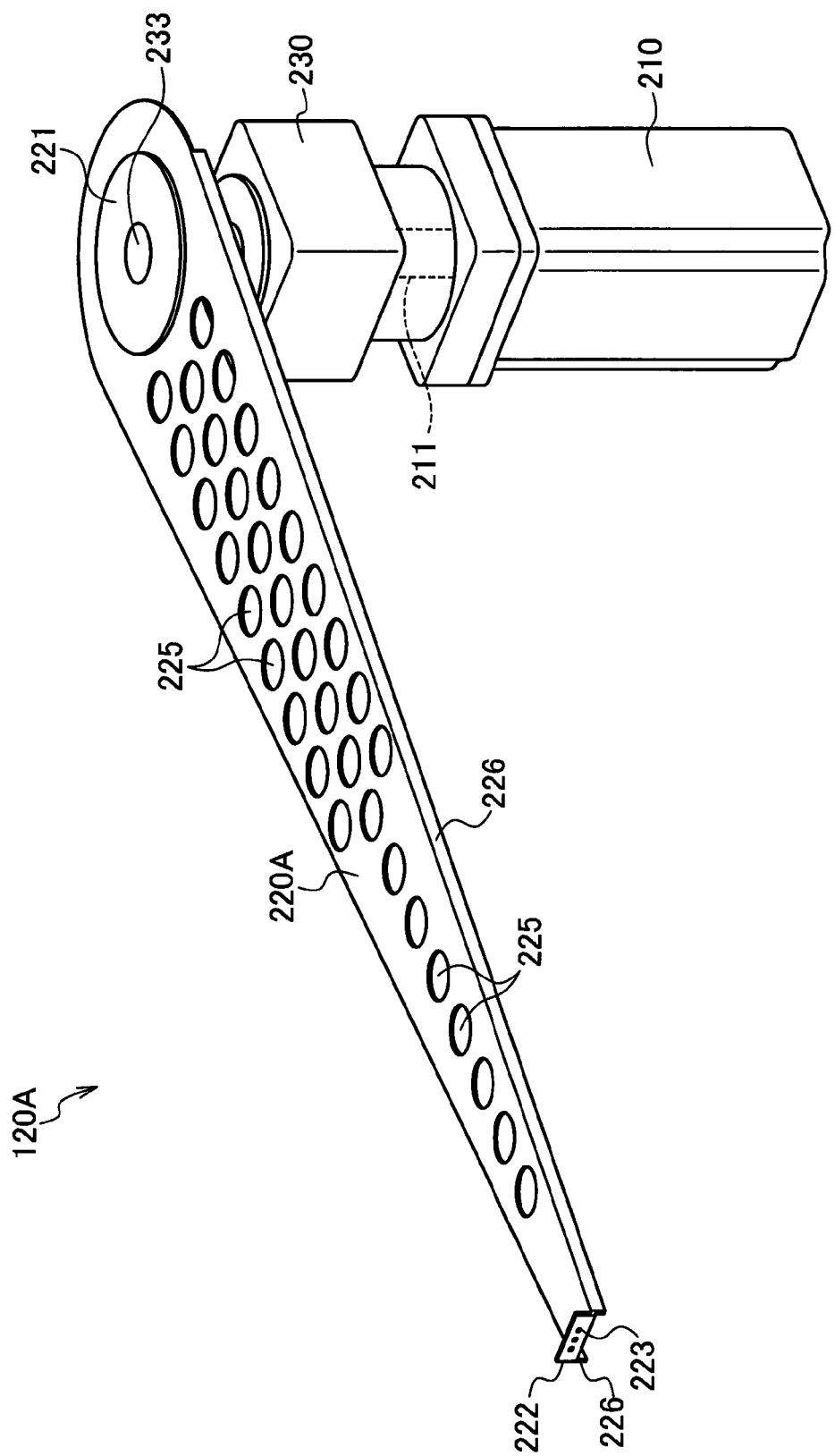
FIG. 8 is a perspective view showing a swing guide mechanism 120A according to a modified example.

FIG. 8 is a perspective view showing the swing guide mechanism 120A according to the modified example. As shown in FIG. 8, an arm member 220A forming the swing guide mechanism 120A is in a plate shape which is tapered from a base 221 towards a tip end portion 222. The arm member 220A has multiple circular holes 225 provided therein. In addition, an outline edge 226 in a shorter direction of the arm member 220A is bent towards a side, of the arm member 220, on which the motor 210 is positioned.

According to the modified example, by providing the multiple circular holes 225 in the arm member 220A, an increase in weight of the arm member 220 can be reduced even when a material which is considered to be heavier than a carbon fiber or the like (for example, a stainless steel plate) is used for the arm member 220A.

In addition, the outline edge 226 of the arm member 220A is bent, so that the strength of the arm member 220A is improved as compared with the case where the outline edge 226 is not bent.

Here, the description has been given in which the multiple circular holes 225 are provided in the arm member 220A and the outline edge of the arm member 220A is bent. However, the configuration is not limited to this, and, as a matter of course, it is only needed to form any one of these.

In addition, the circular holes 225 are described to be in circular shapes. However, the configuration is not limited to this. For example, the circular holes 225 may be polygonal such as triangular or quadrangular. The shape, arrangement, and number of the circular hole 225, for example, are not particularly limited and are properly selectable depending on a purpose thereof.

Furthermore, the outline edge of the arm member 220A is described to be bent towards the side, of the arm member 220, on which the motor 210 is positioned. However, the configuration is not limited to this. The outline edge of the arm member 220A may be bent towards a side of the arm member 220 opposite to the side thereof on which the motor 210 is positioned.

Other Embodiments

As described above, the contents of the present invention have been disclosed by using the embodiment of the present invention. It should not be understood that the description and drawings constituting the disclosure of the present invention are intended to limit the present invention. Various alternative embodiments, examples, and operational techniques will be apparent for a person skilled in the art from the disclosure.

For example, the embodiment of the present invention may be changed as follows. Specifically, the manufacturing method of an absorbent article and the elastic member fixing apparatus are not limitedly applicable to the absorbent article 1 (so-called a disposable diaper) provided with the front waistline region 10, the back waistline region 20, the crotch region 30, and the like, but is applicable to various articles such as disposable gowns for medical use and disposable wears for sports.

In addition, the elastic member, which is a component forming the absorbent article 1, has been described as being formed of an elastic filiform rubber or the like. However, the elastic member is not limited to this and may be formed of a flat rubber, a sheet-like rubber, or the like. Moreover, the elastic member does not have to be a rubber. For example, the elastic member may be resilient or elastic fibers such as polyester and polyurethane. The elastic member may be an elastic fiber other than these fibers. Some of these fibers may be used by being stranded.

In addition, the lengths of the arm members 220 of the first swing guide mechanism 200A and the second swing guide mechanism 200B are described to be different from each other. However, the configuration is not limited to this but the lengths may be same.

In addition, the program operating the motor 210 of the first swing guide mechanism 200A is described to be different from the program operating the motor 210 of the second swing guide mechanism 200B. However, the configuration is not limited to this, and the program operating the motor 210 of the first swing guide mechanism 200A may be same as the program operating the motor 210 of the second swing guide mechanism 200B. That is, the predetermined extension magnification or the layout in the front leg gather 6a may be same as the predetermined extension magnification or the layout in the back leg gather 6b.

In addition, the arm member 220 is described to be formed of a stainless steel plate. However, the configuration is not limited to this. For example, the arm member 230 may be formed of a composite material obtained by compounding a fiber and a resin, such as a synthetic fiber such as a carbon fiber or a polyamide fiber, a metal fiber such as a titanium fiber, a glass fiber, semisynthetic fiber, or natural fiber and a thermoplastic synthetic resin or thermosetting synthetic resin.

In addition, the insertion hole 223 into which the leg gather 6 is inserted is described to be formed in the tip end portion 222 of the arm member 220. However, the configuration is not limited to this. The tip end portion 222 only needs to guide the leg gather 6. For example, a U-shaped groove may be formed.

In addition, the speed reducer 230 is described to be formed of the planet gear mechanism (so-called, the planetary gear structure). However, the configuration is not limited to this and may be any as long as the rotational speed ($V_3$) of the arm member 220 can be made slower than the rotational speed ($V_2$) of the rotational shaft 211 of the motor 210. For example, the speed reducer 230 includes a warm gear speed reducer, a roller gear speed reducer, or the like.

Moreover, the speed reducer 230 is described to be directly connected with the rotational shaft 211 of the motor 210 and the base 221 of the arm member 220. However, the configuration is not limited to this. The speed reducer 230 may be indirectly connected with the rotational shaft 211 of the motor 210 and the base 221 of the arm member 220.

In addition, the rotational shaft 233 of the speed reducer 230 (that is, the rotational shaft of the sun gear 231) and the rotational shaft 211 of the motor 210 are described to be coaxially positioned. However, the configuration is not limited to this. The rotational shaft 233 of the speed reducer 230 and the rotational shaft 211 of the motor 210 may be arranged offset from each other.

In this manner, as a matter of course, the present invention includes various embodiments which are not described herein. Accordingly, the technical scope of the present invention is defined only by the particular matters contained in the scope of claims which is appropriate from this disclosure.

What is claimed is:

1. A method of manufacturing an absorbent article which includes a front waistline region, a back waistline region, and a crotch region positioned between the front waistline region and the back waistline region and has an elastic member provided at least partially in a cross direction crossing a predetermined direction, in the front waistline region, the back waistline region, and the crotch region, the manufacturing method comprising the steps of:
conveying in the predetermined direction a web in which components forming one part of the absorbent article are sequentially arranged;
swinging the elastic member by using a guide arm unit guiding the elastic member, at a predetermined cycle in the cross direction crossing the web being conveyed in the predetermined direction; and
pressing, between one pair of press rollers, the web on which the elastic member is arranged,
wherein the guide arm unit includes
a motor with a rotational shaft;
an arm member guiding the elastic member to a predetermined position on the web in the cross direction; and
a speed reducer provided between the rotational shaft and a base of the arm member to make a rotational speed of the arm member slower than a rotational speed of the rotational shaft,
wherein
the speed reducer includes a sun gear positioned in a center of the speed reducer and multiple planet gears revolvable and rotatable around the sun gear, the multiple planet gears having a revolution shaft,
the rotational shaft of the motor is directly connected with said sun gear,
the revolution shaft of the multiple planet gears is directly connected with the base of the arm member, and
the revolution shaft of the multiple planet gears and the rotational shaft of the motor are coaxially positioned.

2. The method of manufacturing an absorbent article according to claim 1, wherein the speed reducer reduces a rotational speed of a tip of the arm member from which the elastic member is fed, down to 1/S of the rotational speed of the rotational shaft of the motor, and the S is no fewer than 1, no more than 8.

3. The method of manufacturing an absorbent article according to claim 2, wherein the S is a natural number.

4. The method of manufacturing an absorbent article according to claim 1, wherein a length of the arm member is no less than 450 mm, no more than 700 mm.

5. The method of manufacturing an absorbent article according to claim 1, wherein a weight of the arm member is no less than 150 g, no more than 500 g.

6. The method of manufacturing an absorbent article according to claim 1, wherein an amplitude of the tip end portion of the arm member in the cross direction is no less than 150 mm, no more than 420 mm.

7. The method of manufacturing an absorbent article according to claim 1, wherein the arm member is formed of a metal steel plate.

8. The method according to claim 1, wherein said arm member includes a plurality of holes.

9. The method according to claim 1, wherein the arm member has an outline edge that is bent towards a side of the arm member on which the motor is positioned.

10. The method according to claim 1, wherein said guide arm unit include a first swing guide mechanism and a second swing guide mechanism positioned in parallel in the cross direction,
said first swing guide mechanism and the second swing guide mechanism include a first base plate and a second base plate, respectively, which are positioned in different positions in the predetermined direction with respect to the pair of press rollers,
said arm member includes a first arm member associated with the first swing guide mechanism and a second arm member associated with the second swing guide mechanism, and
said first arm member and the second arm member include a first tip end portion and a second tip end portion, respectively, which are positioned in a same position in the predetermined direction.

11. The method according to claim 10, wherein
the first arm member has an amplitude which defines a first curve in a swinging action of the first arm member,
the second arm member has an amplitude which defines a second curve in a swinging action of the second arm member, and
said first curve crosses the second curve.

12. An apparatus for manufacturing an absorbent article, said manufacturing apparatus comprising:
a guide arm unit for guiding an elastic member on a web in which components forming one part of the absorbent article are subsequently arranged, the absorbent article provided with a front waistline region, a back waistline region, and a crotch region positioned between the front waistline region and the back waistline region,
wherein the guide arm unit includes
a motor with a rotational shaft;
an arm member for guiding the elastic member to a predetermined position on the web in a cross direction; and a speed reducer provided between the rotational shaft and a base of the arm member to make a rotational speed of the arm member slower than a rotational speed of the rotational shaft, wherein the speed reducer includes a sun gear positioned in a center of the speed reducer and multiple planet gears revolvable and rotatable around the sun gear, the multiple planet gears having a revolution shaft, the rotational shaft of the motor is directly connected with said sun gear, the revolution shaft of the multiple planet gears is directly connected with the base of the arm member, and the revolution shaft of the multiple planet gears and the rotational shaft of the motor are coaxially positioned.

13. The apparatus according to claim 12, wherein said arm member includes a plurality of holes.

14. The apparatus according to claim 12, wherein the arm member has an outline edge that is bent towards a side of the arm member on which the motor is positioned.

15. The apparatus according to claim 12, wherein said guide arm unit include a first swing guide mechanism and a second swing guide mechanism positioned in parallel in the cross direction, said first swing guide mechanism and the second swing guide mechanism include a first base plate and a second base plate, respectively, which are positioned in different positions in a machine direction substantially perpendicular to the cross direction with respect to a pair of press rollers for pressing the elastic member on the web, said arm member includes a first arm member associated with the first swing guide mechanism and a second arm member associated with the second swing guide mechanism, and said first arm member and the second arm member include a first tip end portion and a second tip end portion, respectively, which are positioned in a same position in the predetermined direction.

16. The apparatus according to claim 15, wherein the first arm member has an amplitude which defines a first curve in a swinging action of the first arm member, the second arm member has an amplitude which defines a second curve in a swinging action of the second arm member, and said first curve crosses the second curve.

* * * * *